United States Patent [19]

Fischer

[11] Plant 4,934

[45] Nov. 9, 1982

[54] AFRICAN VIOLET NAMED BLUEBIRD

[75] Inventor: Arnold W. Fischer, Hanover, Fed. Rep. of Germany

[73] Assignee: Pan-American Plant Company, Parrish, Fla.

[21] Appl. No.: 252,317

[22] Filed: Apr. 9, 1981

[51] Int. Cl.[3] ..... A01H 5/00

[52] U.S. Cl. ..... Plt./69

[58] Field of Search ..... Plt./69

*Primary Examiner*—James R. Feyrer

*Attorney, Agent, or Firm*—Chas. W. Rummler

[57] ABSTRACT

A new and distinct African Violet cultivar distinguished by its vigorous growth and profusion of blooms of a dark violet color borne on sturdy, erect peduncles, as in a bouquet above the medium green foliage of the plant. The flower is zygomorphic with three larger and two smaller petals which have ruffled edges and excellent keeping quality.

3 Drawing Figures

BACKGROUND OF THE NEW PLANT

This new African Violet variety originated as a seedling of unknown parentage growing among a field of plants in one of my greenhouses at Hanover, West Germany. This plant was discovered by me in 1975 and was selected for testing because of its profuse production of zygomorphic flowers of a dark violet color borne as in a bouquet above the plant foliage. This new plant was reproduced by me, by means of cuttings from the parent, in my greenhouse at Hanover with very satisfactory results and subsequently, this plant was propagated through a series of generations, by means of cuttings, and it was found that the novel characteristics of this plant would hold true from generation to generation and appeared to be firmly fixed.

This plant is now being propagated on a commercial scale at West Chicago, Ill., and at Parrish, Fla., U.S.A., by means of leaf cuttings.

DESCRIPTION OF THE DRAWINGS

This new violet plant is illustrated by the accompanying drawings, of which sheet 1 is a full color photographic view of a potted plant in full bloom, and sheets 2 and 3 are prints of machine copies of the front and back sides, respectively, of typical leaves of this plant.

DESCRIPTION OF THE NEW PLANT

The following is a detailed description of the new African Violet plant based upon observations made in greenhouse at West Chicago, Ill., U.S.A., the color designations being according to The R.H.S. Colour Chart published by The Royal Horticultural Society of London, England.

THE PLANT

Origin: Seedling.
Parentage: Unknown.
Classification:
- *Botanic.*—*Saintpaulia ionantha.*
- *Commercial.*—African Violet.

Form: Compact and of rosette shape.
Growth: Strong and vigorous.
Growth rate: Rapid.
Foliage:
- *Quantity.*—Moderate; about 15 leaves.

- *Size of leaf.*—Length — From insignificant to about 70 mm. Width — From insignificant to about 68 mm.
- *Shape of leaf.*—Oval, with acute tip, oblique base, and repand margin.
- *Appearance.*—Glossy.
- *Ribs and veins.*—Pinnate with rachis length varying from insignificant to about 70 mm.
- *Color.*—Upper Side — 137A. Under Side — 138D.
- *Petioles.*—Length — Varying from insignificant to about 110 mm.

THE BUD

Form: Globular.
Size: Average, with various lengths and diameters at time of opening.
Opening rate: Typical violet.
Color of petals:
- *When sepals first divide.*—86C.
- *When petals begin to unfurl.*—93A.

Sepals:
- *Number.*—Five.
- *Shape.*—Lanceolate and branched.
- *Color.*—Inside — 148B. Outside — 148C.
- *Striae.*—None.

Calyx:
- *Size.*—Small.
- *Shape.*—Calyx splits to star shape.
- *Aspect.*—Hairy.

Flower stem:
- *Length.*—From insignificant to about 90 mm.
- *Aspect.*—Hairy.
- *Strength.*—Erect and rigid.
- *Color.*—147C.

THE FLOWER

Blooming habit: Intermittent.
Flowering: Profusely.
Size of flower: Medium; about 30 to 40 mm. in diameter.
- *Borne.*—As a cyme.
- *Shape.*—Cup-shaped when bloom first opens; becoming flat as the bloom matures.

Petalage:
- *Number of petals.*—Five in sympetalous arrangement.
- *Form.*—Rotate-zygomorphic with sinuate margins and rounded apex.

*Texture.*—Soft.

*Aspect.*—Satiny.

*Color.*—Upper surface — 93A. Reverse side — 94C.

Petaloids: None to few in number and of various sizes.

*Color.*—93A.

Flower Stem:

*Character.*—Strong and upright.

*Length.*—From insignificant to about 90 mm.

Discoloration after full bloom: The flowers fade to 93C.

Persistence: The flowers hang on and dry.

Fragrance: None.

Lasting quality: From 10 to 20 days on the plant.

REPRODUCTIVE ORGANS

Stamens:

*Anthers.*—Two in number and in monadelphous arrangement. Size: 3 by 3 mm. square. Color: Yellow.

*Filaments.*—Length: About 3 mm. Color: Whitish yellow.

*Pollen.*—Color — Yellow.

Pistils:

*Number.*—One.

*Style.*—Length: About 8 mm. Color: White.

*Stigma.*—Color — 93A.

Ovaries: Hypogynous and tomentose.

This African Violet cultivar is distinguished by its profuse production of flowers of a dark violet color borne as a bouquet above a plant of rosette form. This new plant is also distinguished by its vigorous growth habit and the excellent keeping quality of its flowers.

I claim:

1. A new and distinct African Violet cultivar, substantially as herein shown and described, characterized by its profuse production of flowers of a dark violet color.

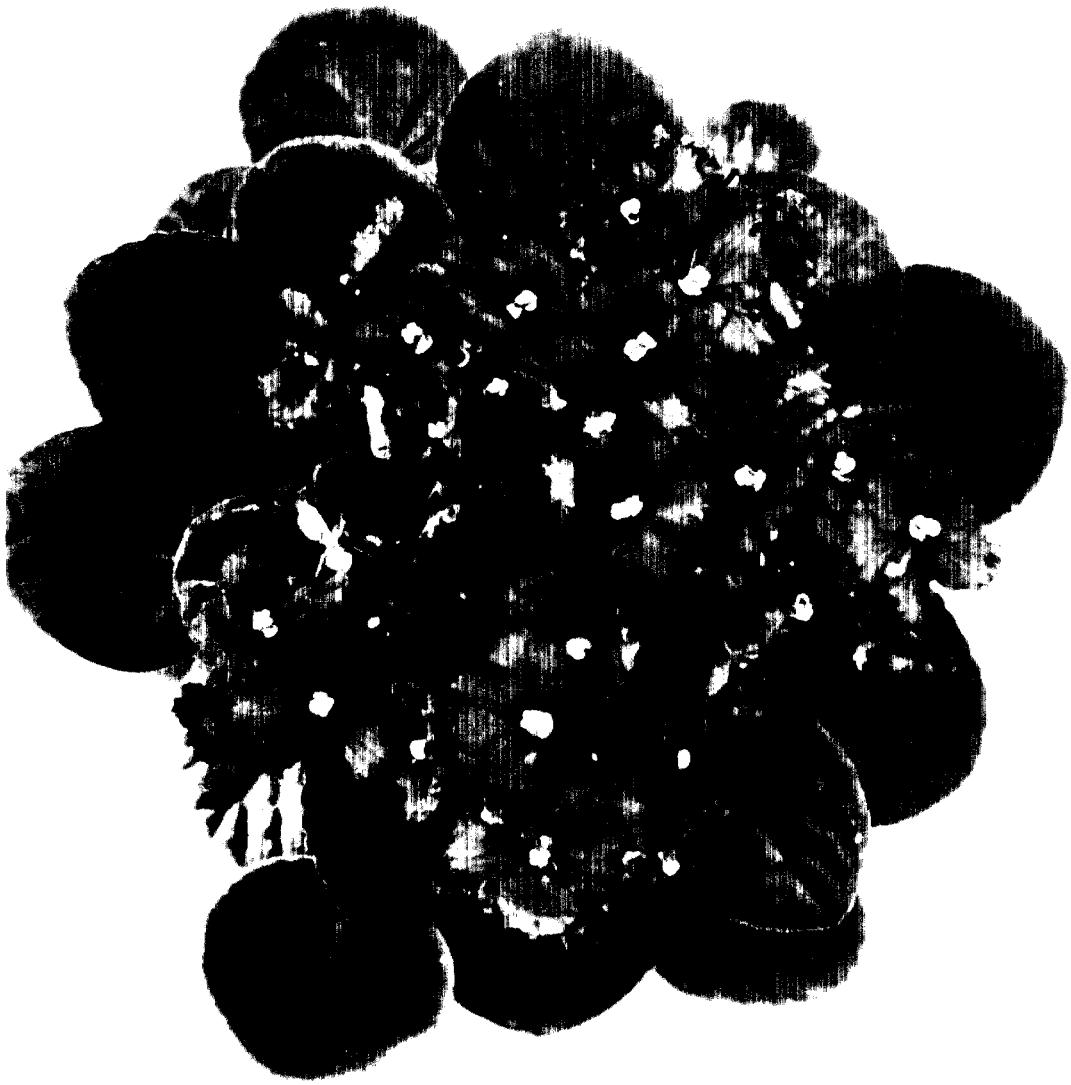

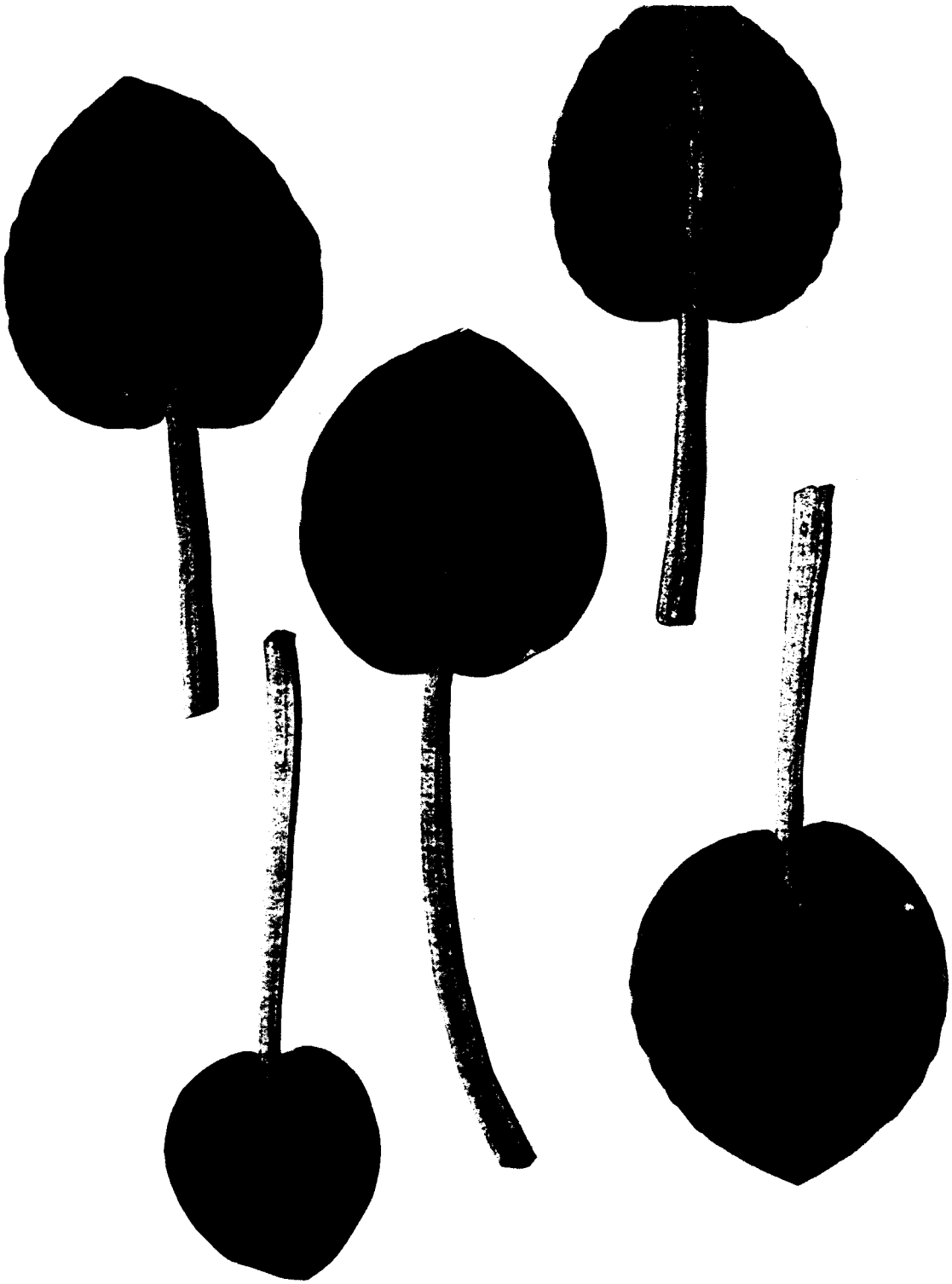

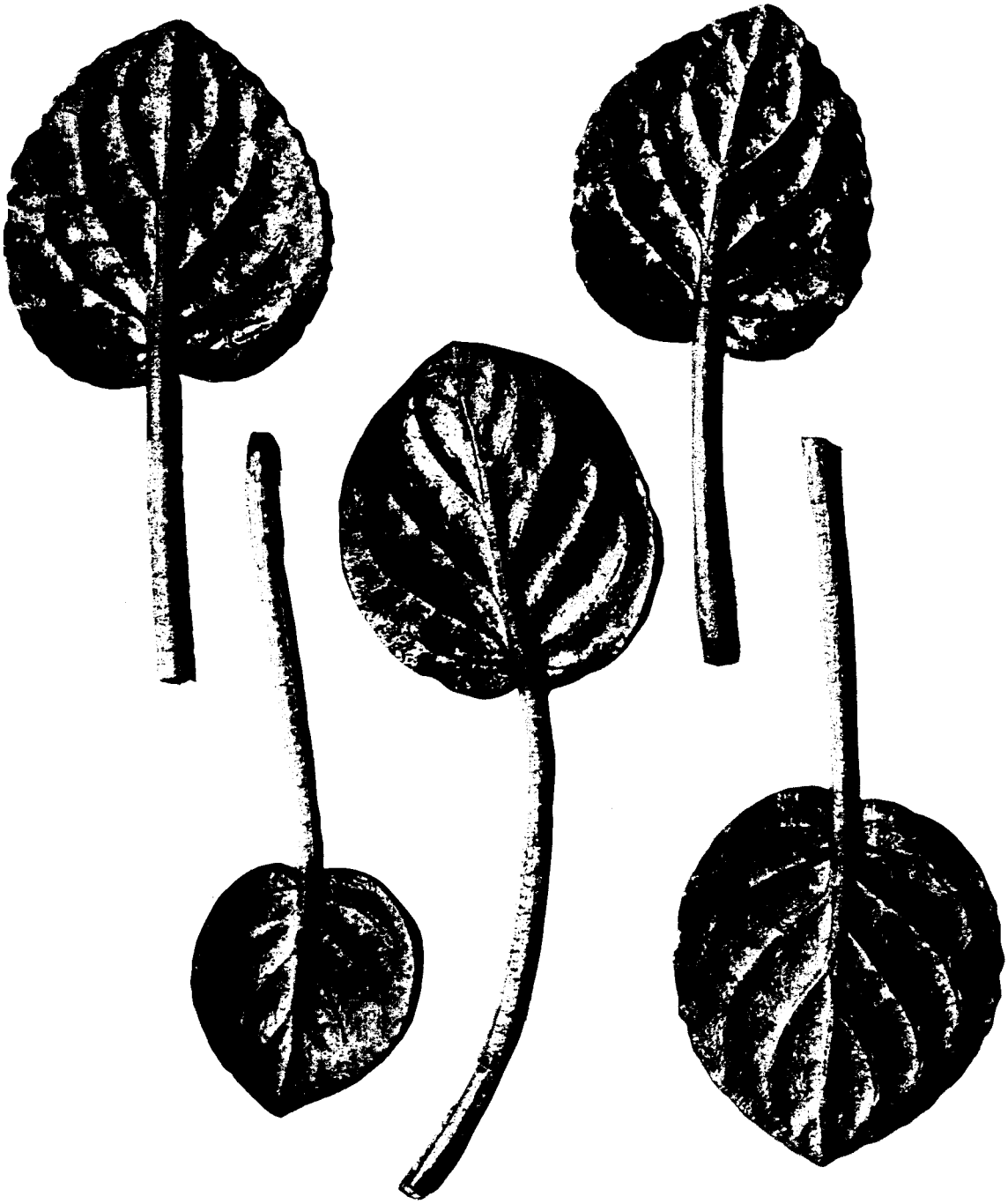

* * * * *